United States Patent
Hughes

[19]

[11] Patent Number: 5,829,429
[45] Date of Patent: Nov. 3, 1998

[54] ACOUSTIC RESPIRATORY THERAPY APPARATUS

[76] Inventor: Arthur R. Hughes, 2736 S. Uravan, Aurora, Colo. 80013

[21] Appl. No.: 843,745

[22] Filed: Apr. 21, 1997

[51] Int. Cl.$^6$ .................................................. A61M 15/00
[52] U.S. Cl. .......................... 128/200.24; 601/41; 482/13
[58] Field of Search ........................ 128/200.24, 202.28, 128/202.29; 601/41, 43; 482/13

[56] References Cited

U.S. PATENT DOCUMENTS

| | | | |
|---|---|---|---|
| 2,918,917 | 12/1959 | Emerson | 601/41 |
| 3,037,497 | 6/1962 | Roberson | 128/202.29 |
| 3,158,152 | 11/1964 | Bloom | 128/202.29 |
| 3,628,280 | 12/1971 | Nave | 601/41 |
| 3,863,914 | 2/1975 | O'Connor | 601/41 |
| 4,054,134 | 10/1977 | Kritzer | 482/13 |
| 4,062,358 | 12/1977 | Kritzer | 482/13 |
| 4,221,381 | 9/1980 | Ericson | 482/13 |
| 4,275,722 | 6/1981 | Sorenson | 128/200.24 |
| 4,297,999 | 11/1981 | Kitrell | 601/41 |
| 4,349,015 | 9/1982 | Alferness | 601/41 |
| 4,813,403 | 3/1989 | Endo | 128/32 |
| 5,018,517 | 5/1991 | Liardet | 128/200.24 |
| 5,451,190 | 9/1995 | Liardet | 482/13 |
| 5,569,122 | 10/1996 | Cegla | 482/13 |
| 5,628,305 | 5/1997 | Melker | 128/202.29 |
| 5,647,345 | 7/1997 | Saul | 128/200.24 |

OTHER PUBLICATIONS

General Physiotherapy, Inc. *Flimm Fighter*™ *Operating Instruction Manual*, 1993.

American Biosystems, *The ThAIRaphy*™ *Vest Clearance System*, Dec. 1995.

Med Systems, *Med Model 2500 Fluid Flo Percussor*, Jan. 1995.

*Primary Examiner*—Aaron J. Lewis
*Attorney, Agent, or Firm*—John R. Wahl; Holland & Hart LLP

[57] ABSTRACT

A respiratory therapeutic device for actively loosening and breaking up phlegm in a user's lungs and bronchial and tracheal passages while a user is breathing through the device is disclosed which comprises a housing containing a base portion and a cap portion forming at least a portion of a sonic coupling chamber having a plurality of breathing holes therethrough and adapted to be held in a patient's mouth. The base portion contains an audio generator behind a sanitary flexible diaphragm separating the portions. The generator preferably includes a power supply and a pulsed audio signal generator connected to the speaker. The audio signal generator may be adjusted by the user as to tone pitch and tone burst repetition rate to optimally loosen accumulated phlegm in the user's lungs during unit operation.

20 Claims, 3 Drawing Sheets

ACOUSTIC RESPIRATORY THERAPY APPARATUS

BACKGROUND OF THE INVENTION

1. Field of the Invention

This invention generally relates to respiratory devices and more particularly to a vibrating device which assists in breaking up and dislodging accumulated fluids and solids generated in a user's lungs.

2. Description of the Related Art

People who have lung diseases such as cystic fibrosis, bronchiactasis and chronic bronchitis have a difficult time breaking up, dislodging, and expelling mucus and phlegm which develops in the lungs. The presence of this material in the lungs and bronchial and tracheal passages provides an excellent media for growth of bacteria. For treatment of the condition, rotation of antibiotics is used to treat the bacterial infections that result. Percussive therapy and the use of a mechanical device called a flutter valve are used to help the patient dislodge this mucus material.

Such percussive devices are disclosed in U.S. Pat. Nos. 5,018,517 and 5,451,190 to Liardet. This device, as are other flutter valve devices available and in use today is self powered. That is, the patient exhales into the device which sets up vibrations which feed back through the patient's air ways to break up and dislodge the phlegm. However, this activity is energy consumptive and very draining to the patient. Often, because of a debilitating condition from the effects of pneumonia, for example, the patient has great difficulty blowing into these self powered mechanical devices with sufficient force to achieve any substantive success at dislodging accumulated phlegm.

An active vibratory device is disclosed in U.S. Pat. No. 4,813,403 to Endo. This device comprises an oscillator for generating an electrical signal at a frequency optimally effective for the patient, an audio amplifier, and a speaker connected, through a closed gas volume, to a vibratory diaphragm which is placed against the patient's body, typically the patient's chest or back. The vibration is then transferred from the speaker, through the closed gas volume, to the diaphragm, then to the surface of the patient's body to treat such problems as shoulder discomfort, arthritis, asthmatic spasms and improve blood circulation. The major disadvantage with this approach when the lungs are the target is that by placing the unit on a user's back or chest, the intervening body tissue substantially attenuates the vibration before it reaches the target area of the lungs and bronchial tubes.

Therefore there is an urgent need for a device that can efficiently and effectively transmit acoustic vibrations to the sites of phlegm buildup in the patient's lungs. There is also a need for a device which does not usurp the patient's energy during device operation so that this energy can be reserved for effective expulsion of dislodged phlegm.

SUMMARY OF THE INVENTION

The apparatus in accordance with the present invention meets the above identified needs.

It is thus an object of the invention to provide a powered apparatus for directly assisting a patient in breaking up phlegm and mucus plugs in the alveoli and bronchial tubes.

It is another object of the invention to provide an acoustical apparatus that the patient may adjust to achieve optimal breakup of phlegm and mucus plugs.

It is another object of the invention to provide a powered apparatus which a patient can use while breathing in a normal manner yet provide efficient transmission of vibrations directly through the patient's airways to effectively breakup and loosen phlegm and mucus buildup in the patient's lungs.

These and other objects and features of the invention are achieved by an electrically powered apparatus which comprises a housing, a power supply, a variable frequency oscillator and an audio amplifier in the housing connected to the power supply, a speaker connected to the amplifier and facing an elastic diaphragm in the housing forming a portion of a sonic coupling air chamber in the housing, and a passage from the air chamber to a mouthpiece adapted to be held in a user's mouth while breathing through the air chamber. The housing has a plurality of relatively small holes around the peripheral wall of the chamber to permit the user's breath to exit the sonic coupling chamber and through which the user can draw fresh air into his or her lungs during operation of the apparatus.

The mouthpiece of the apparatus is inserted into the user's mouth and the user breathes normally through his or her mouth. The user turns on the apparatus and the speaker produces a series of sonic pulses which are directed into the user's lungs through the passage. The apparatus includes controls for varying the repetition rate and the frequency of the transmitted sound pulses so that the user can select the particular optimum combination for his or her condition. The apparatus may be used for as long as needed. The user need only remove the mouthpiece while coughing to expel loosened phlegm and mucus. Thus the apparatus of the invention may be either battery powered by a few conventional batteries or may be powered from normal house current. The apparatus may also include rechargeable batteries for use while traveling. These and other features and advantages will become more apparent from a reading of the following detailed description when taken in conjunction with the drawing figures.

DETAILED DESCRIPTION OF THE INVENTION

Figure 1:
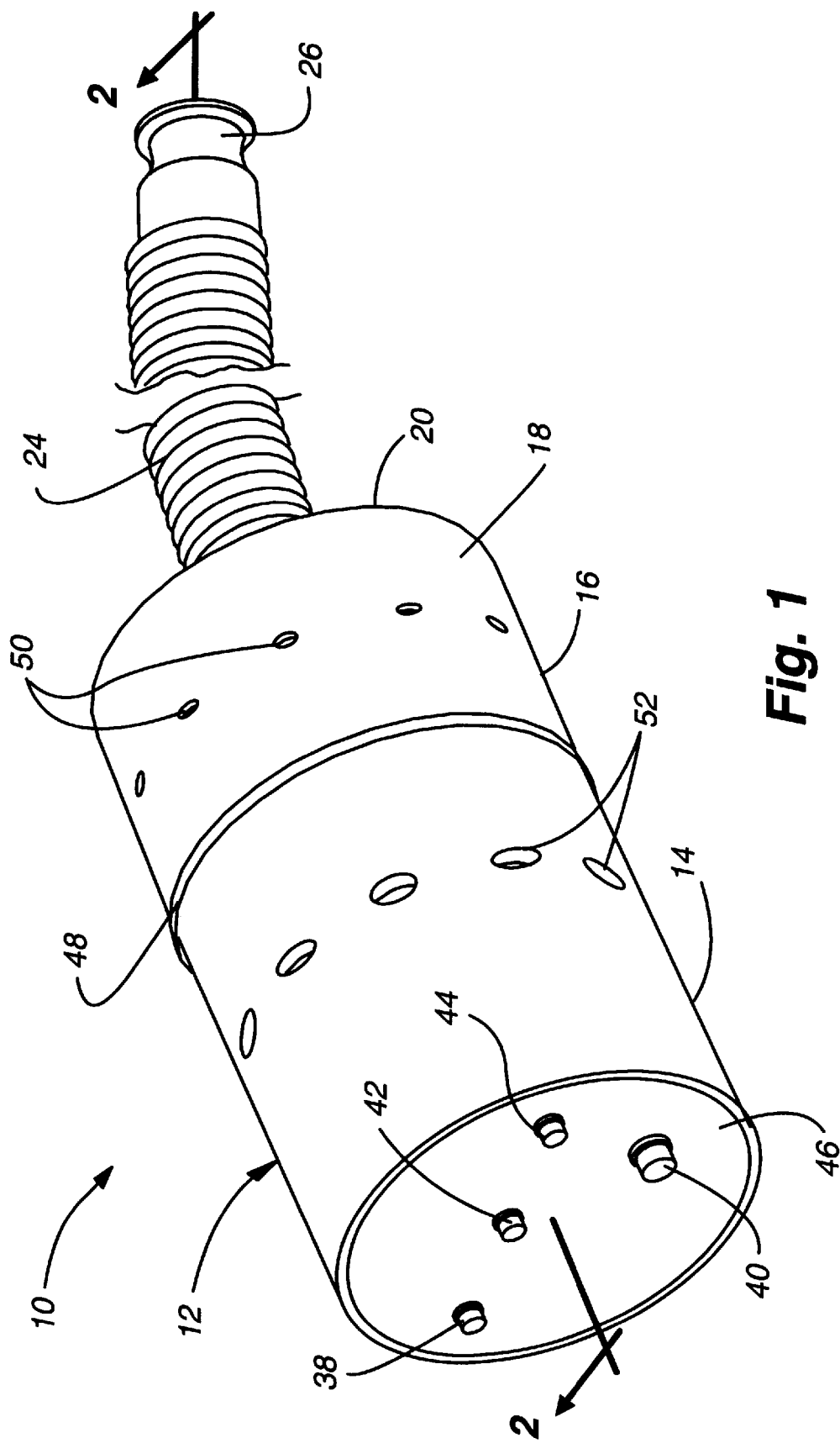
FIG. 1 is a perspective view of the apparatus in accordance with the present invention.
Figure 2:
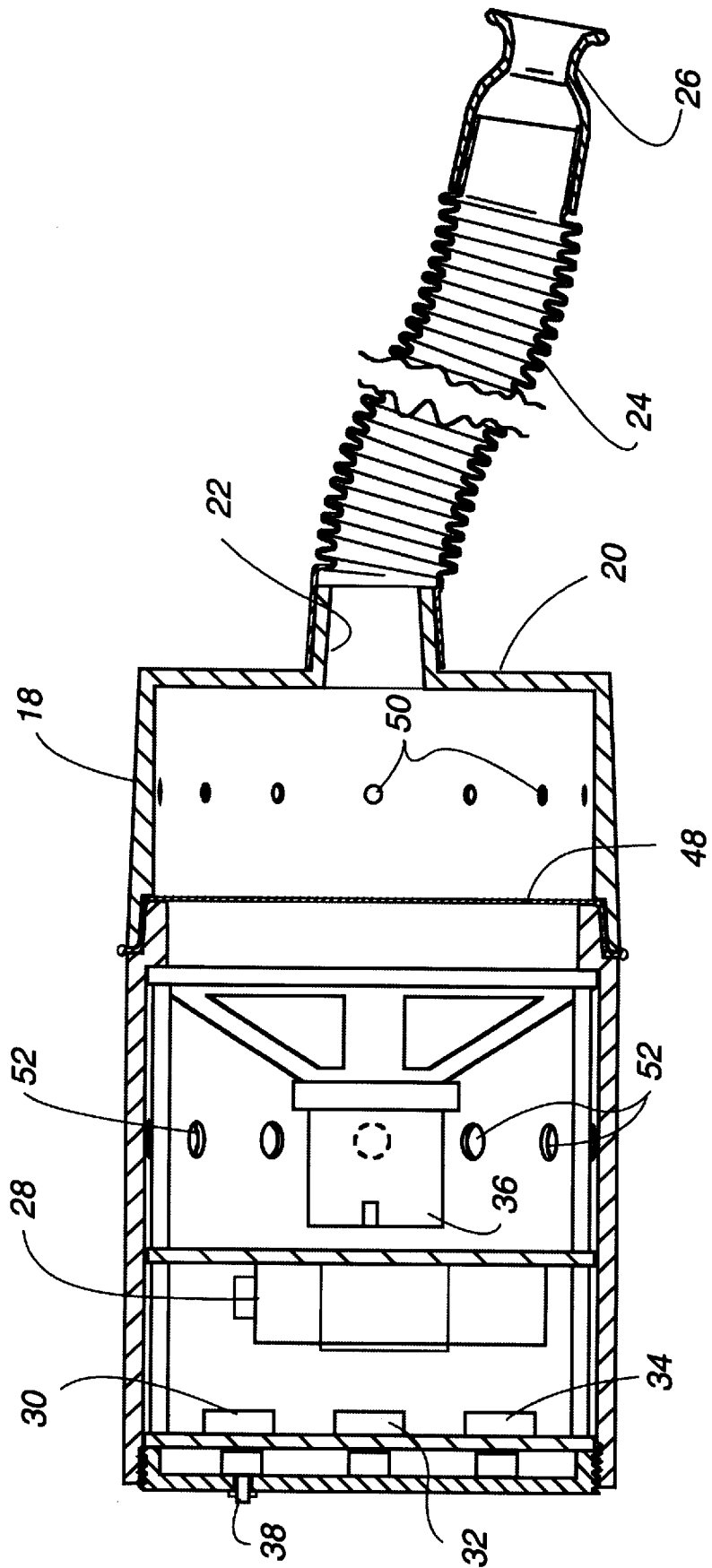
FIG. 2 is a sectional view of the apparatus in accordance with the present invention shown in FIG. 1.
Figure 3:
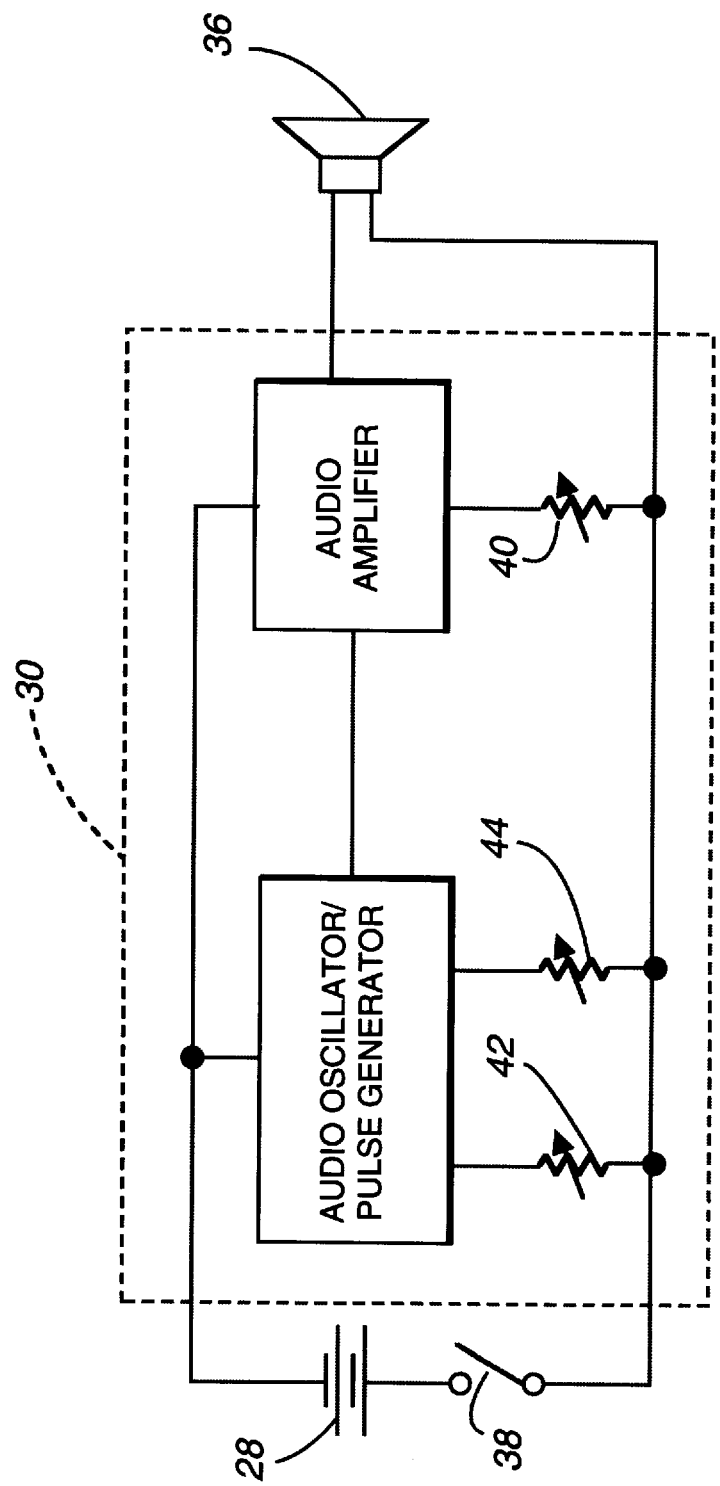
FIG. 3 is a block diagram of the circuit in the apparatus shown in FIG. 1.

Referring to FIG. 1, an apparatus 10 is shown in a perspective view. The apparatus 10 comprises a generally cylindrical housing 12 that has a bottom or base tubular portion 14 and a tubular cap portion 16. The cap portion 16 has a tubular side wall 18 and a disk shaped end wall 20 having a central aperture 22 therethrough connected to one end of a flexible breathing tube 24. The other end of the flexible tube 24 preferably has a preferably semi-rigid mouthpiece 26 designed to be held in the user's mouth between the teeth.

The bottom tubular portion 14 contains a battery power supply 28, a circuit board 30 containing an audio oscillator circuit 32 and an audio amplifier circuit 34 thereon, and supports an audio speaker 36 connected to the output of the audio amplifier 34. An on/off switch 38, volume control 40, frequency control 42, and a repetition rate control 44 are accessible through apertures in a disk shaped bottom plate 46 closing the bottom or base of the tubular portion 14.

The base tubular portion 14 and the tubular cap portion 16 are preferably telescopically fit together. A replaceable elastic diaphragm 48 is captured therebetween and captured by the telescoping ends of the tubular portions 14 and 16. The purpose of the diaphragm is primarily to prevent contaminants from contacting the speaker cone and other components in the lower tubular portion 14 of the housing 12. Accordingly, the diaphragm 48 may be reusable or disposable. The cap portion 16, the cone of the speaker 36, the flexible tube 24, and the mouthpiece 26 together define an acoustic coupling chamber 27 which couples the speaker 36 to the user's airways in use.

During installation of the housing components, the diaphragm 48 is preferably stretched over the bottom end of the cap portion 16 and then the cap portion 16 is slipped over the open speaker end of the bottom portion 14. In this way, when the apparatus is disassembled after use, the cap portion 16, diaphragm 48, tube 24 and mouthpiece 26 are removed as an assembly. The component parts may then be disassembled and cleaned or sterilized.

Alternatively, the diaphragm 48 may be first installed on the bottom portion 14 and/or the cap portion 16 may alternatively be sized to fit within the open end of the bottom portion 14. The diaphragm 48 may optionally be an annular disk of thin elastic material with a relatively rigid rim which fits snugly within either the cap portion or the bottom portion 14. In any event, the diaphragm 48 is placed so as to shield the speaker cone from any contaminants that may be exhaled by the user of the apparatus of the invention but still transmit sound vibrations therethrough into the cap portion 16.

The acoustic coupling chamber 27 may alternatively be formed more compactly by eliminating the tube 24 and connecting the mouthpiece 26 directly to the cap portion 16. Alternatively, the cap portion 16 with the mouthpiece 26 may be integrally formed as a one piece molded structure without the tube 24 at all. In this instance, the cap portion 16 and mouthpiece 26, together with the cone of the speaker 36, define the coupling chamber 27. Since the diaphragm 48 is elastic, supple and flexible, its presence is virtually transparent to the sound transmission from the speaker 36 through the sonic coupling chamber 27 into the patient's airways during use.

The speaker 36 is preferably sized so that the outer diameter of the cone is approximately the same as the internal diameter of the tubular bottom portion 14. The speaker 36 nests in the tubular bottom portion 14 and the cone faces the cap portion 16 and the diaphragm 48. The speaker preferably is of a compact, high efficiency design so as to minimize power drain. The power output of the speaker should preferably be within a range of 2 to 5 watts. Speaker power levels of more than 5 watts may tend to damage bronchial or lung tissue and therefore should preferably be avoided. This power limitation may optionally be designed into the amplifier circuitry to preclude inadvertent over stimulation of sensitive lung tissues.

A plurality of holes 50 are provided preferably through the tubular side wall of the cap portion 16 in order for the user to breathe through the sonic coupling chamber 27 while using the apparatus 10 in accordance with the present invention. Each of these holes 50 has a diameter that is much smaller than the wavelength of the sounds being generated by the speaker, on the order of less than 0.5 inch. For example, the wavelength of a 60 hertz sound is 18 feet. The wavelength of a 1000 hertz sound is 1.09 feet, and 10,000 hertz is 0.1 foot. The hole diameter is preferably on the order of 0.050 inches to 0.075 inches, or 0.004 feet. The most effective frequencies of interest are less than 10,000 hertz. The apparatus may have any frequency range, however, a range between 10 hertz and 10,000 hertz is preferred. Users will most likely utilize frequencies between 20 to 300 hertz. Therefore, for most frequencies of interest, the hole diameter is at least one to two orders of magnitude smaller than the wavelengths of the sounds produced. Since these holes 50 are substantially smaller than the wavelengths of interest, little sound pressure will be lost from the chamber 27 even when their combined effect is considered. However, these holes are important because they permit the user to breath normally while using the apparatus 10.

The holes 50 may be located anywhere in the walls of the sonic coupling chamber 27. For example, they may alternatively be located in the side wall 18, the end wall 20, the tube 24 or the mouthpiece 26. However, the side wall 18 or end wall 20 is preferred. The size of the holes may also be larger than described above, if other means of preventing substantial loss of acoustic pressure waves is provided. For example, the holes 50 may be partially covered by an integral baffle arrangement molded or otherwise formed within the cap portion 16. Other sonic guide and focusing structures may also be provided within cap portion 16 to enhance the sonic pressure pulse transmission into the user's airways and lungs.

The bottom portion 14 also has a plurality of holes 52 in the peripheral tubular wall 54 to permit the speaker to vibrate freely. The size of these holes is not critical. However, a diameter of about 0.25 inches is preferred. The combined area of these larger holes is between about 70% and 100% of the speaker's active projected surface area. The space between the diaphragm 48 and the speaker 36 is a closed space. However, because the diaphragm 48 is very flexible and resilient, made of preferably a very elastic material such as latex or synthetic rubber, little acoustic attenuation results and the sound pulses effectively are transmitted through the diaphragm unimpeded from the speaker 36 through the coupling chamber 27.

The apparatus 10 may be constructed otherwise than as specifically disclosed above and shown with a reference to a preferred embodiment of the invention. Many changes, alterations and modifications may be made without departing from the scope of the invention. For example, the apparatus 10 is shown in a generally cylindrical housing. Other shapes may be utilized as well. The housing may also be telescopically expandable to provide an optimum coupling volume in a particular application or the housing may have an oval cross section or other cross sectional shape. A telescopically adjustable cap portion 16 with respect to base portion 14 would permit the sonic coupling chamber 27 to be tuned to various resonant frequencies in order to achieve optimum sonic pressure pulse delivery to the patient. The mouthpiece 26, tube 24, end wall 22 and side wall 18 may be molded as an integral single unit. The bottom portion 14 may be much more compactly arranged and all components may be packaged with a rechargeable power supply rather than a battery pack or line cord. Also, the electronic components may be implemented by a micro-controller in order to reduce space. The base portion 14 may include an integral pistol grip or other ergonomically desirable shape for the user to grasp during use. Accordingly, the invention is intended to encompass all such variations as will be readily apparent to those skilled in the art and is not limited to the embodiment shown and described above.

What is claimed is:

1. An apparatus for assisting a patient in loosening phlegm collected in such a patient's lungs and bronchial or tracheal passages comprising:

a hollow housing having a cap portion and a base portion, said cap portion forming at least part of a sonic coupling chamber having a plurality of breathing holes therethrough;

an audio signal generator housed within said base portion having a speaker coupled to said cap portion, said generator transmitting sonic pressure pulses into said coupling chamber; and a mouthpiece connected to the cap portion adapted to be held in a patient's mouth thereby coupling the acoustic coupling chamber to such a patient's airways when such a patient breathes through the holes through the chamber in order to transmit said pressure pulses into such a patients airways.

2. The apparatus according to claim 1 wherein the cap portion is removable from the base portion.

3. The apparatus according to claim 2 further comprising an elastic diaphragm between said cap portion and said base portion.

4. The apparatus according to claim 1 wherein said chamber further comprises a flexible tube connected between said cap portion and said mouthpiece.

5. The apparatus according to claim 4 wherein said cap portion has a tubular side wall and a generally disk shaped end wall with an aperture therethrough, said tube being connected to said end wall around said aperture to form a passage through said tube into said cap portion.

6. The apparatus according to claim 5 wherein said holes in said cap portion are located in said tubular side wall.

7. The apparatus according to claim 1 wherein said base portion has a tubular side wall and a disk shaped bottom closing one end of said tubular side wall, said tubular side wall having an opposite end adapted to telescopically engage an end portion of said cap portion.

8. The apparatus according to claim 7 further comprising an elastic diaphragm sandwiched between said cap portion and said base portion to prevent contamination of said speaker and said audio generator in said base portion.

9. The apparatus according to claim 7 wherein said base portion has a plurality of holes therethrough.

10. The apparatus according to claim 7 wherein said audio generator comprises a power supply, an audio oscillator, an amplifier, and a plurality of controls adapted to be operated by the patient to control the power supply, adjust the oscillator frequency, the pulse repetition rate, and the speaker volume.

11. An apparatus for assisting a patient in loosening phlegm collected in such a patient's lungs and bronchial passages comprising:

a hollow housing having a separable cap portion and a separable base portion having a flexible sanitary diaphragm therebetween separating said base portion from said cap portion, said cap portion having a plurality of breathing holes therethrough, said cap portion forming at least a portion of a sonic coupling chamber;

an audio signal generator comprising a power supply, an audio frequency oscillator, and an amplifier connected to a speaker housed within said base portion, said speaker facing toward said cap portion and said diaphragm; and a tube having one end connected into the cap portion and an opposite end adapted to be held in a patient's mouth thereby coupling the acoustic coupling chamber into such a patient's airways when the patient breathes through the tube and through the holes in cap portion.

12. The apparatus according to claim 11 further comprising a plurality of controls on said base portion operable by a patient to selectively control audio frequency and pulse repetition rate.

13. The apparatus according to claim 12 further comprising a control for speaker volume.

14. The apparatus according to claim 12 wherein said controls are accessible through said base portion of said housing.

15. The apparatus according to claim 14 wherein said audio generator produces audio frequencies within a range of about 10 hertz to about 10,000 hertz.

16. The apparatus according to claim 15 wherein said holes have a diameter equal to less than one tenth the wavelength of the audio frequency produced by the audio generator.

17. An apparatus for assisting a patient in loosening phlegm collected in such a patient's lungs and bronchial passages comprising:

a hollow housing having a separable cap portion and a separable base portion, said cap portion having a plurality of breathing holes therethrough;

an audio signal generator comprising a power supply, an audio frequency oscillator, and an amplifier connected to a speaker housed within said base portion, said audio generator being separated from said cap portion by a replaceable flexible diaphragm, said speaker and said cap portion forming an acoustic coupling chamber, said cap portion having a passage therethrough connected to a mouthpiece adapted to couple the chamber into a patient's airways, whereby an audio pulse generated in said audio signal generator is fed through said passage into such a patient's airways while such a patient breathes through said passage and through said holes in said cap portion.

18. The apparatus according to claim 17 wherein said audio signal generator is completely housed within said base portion.

19. The apparatus according to claim 18 wherein said generator includes controls accessible to said patient while using said apparatus to vary audio frequency and pulse repetition rate and turn said generator off and on.

20. The apparatus according to claim 19 wherein said passage comprises a flexible tube having one end connected through an aperture into said cap portion and an opposite end connected to said mouthpiece.

* * * * *